United States Patent

Stoy et al.

[11] Patent Number: 4,480,642
[45] Date of Patent: Nov. 6, 1984

[54] DILATION DEVICE FOR THE CERVIX

[75] Inventors: Vladimir A. Stoy; George P. Stoy, both of Princeton, N.J.

[73] Assignee: Health Products Research, Inc., Somerville, N.J.

[21] Appl. No.: 385,894

[22] Filed: Jul. 26, 1982

[51] Int. Cl.³ ............................................. A61M 29/02
[52] U.S. Cl. ..................................... 128/341; 128/130
[58] Field of Search .............. 128/130, 343, 344, 341; 524/916; 523/121; 604/904, 368

[56]  References Cited
U.S. PATENT DOCUMENTS 3,867,329  2/1975  Halpern et al. ...................... 128/341
3,947,401  3/1976  Stamberger .......................... 524/916
4,056,496  11/1977  Mancini et al. ..................... 524/916
4,237,893  12/1980  Michaels ............................. 128/341

Primary Examiner—Lee S. Cohen
Assistant Examiner—Steven Falk
Attorney, Agent, or Firm—Omri M. Behr

[57] ABSTRACT

There is disclosed a cervical canal swelling device having an essentially cylindrically shaped stem formed in major portion thereof of a dehydrated hydrogel having a swelling capacity of 0.01 to 0.25 and an enforced unimaxial deformation of at least 1.1 and sized to a diameter of from 2 to 10 mm. and to a length of from 35 to 150 mm.

14 Claims, 5 Drawing Figures

DILATION DEVICE FOR THE CERVIX

FIELD OF THE INVENTION

This invention relates to medical devices, and more particularly to a medical device for dilating the cervix.

BACKGROUND OF THE INVENTION

The lower part of uterus communicates with the vagina by a narrow cervical canal. Although the inner diameter of this portion of the anatomical structure varies considerably with age and number of vaginal deliveries, an average diameter of 3–5 mm. is too narrow to allow a variety of medical procedures reaching into the uterus, e.g. to insert a device, such as an IUD, to empty the uterus from products of conception, to remove abnormal inner layer of the uterus by suitable instrument, etc.

With increasing feasibility and availability of new methods for pregnancy termination, the non-traumatic and effective dilation of the cervix remains a major problem. The traditional method of enlarging the cervical canal employs various types of metal dilators. Such procedure require physician's skill and experience, and is often the only painful and most difficult part of abortion procedures. The popularity of metal dilators is declining mainly because of high incidence of cervical uterine injury.

Another method for enlarging the cervical canal uses laminaria tents or inserts i.e., dried sticks of a seaweed growing in cold ocean waters (*Laminaria japonica*). The laminaria inserts swell during several hours in a moist environment with a gradual increase in diameter of up to a value several times larger than the original diameter. The swelling thus applies a slowly increasing pressure onto the cervical canal, and such slow pressure is not painful and it is considered to be atraumatic to the cervical tissue and relatively convenient to the patient.

The use of *Laminaria japonica* has the following shortcomings:

(1) As most of natural materials, it cannot be perfectly sterilized.

(2) Its swelling rate is relatively low so that the insert is left in the cervix, as a rule, for about 24 hours. This is inconvenient to the patient (which must be either hospitalized or make two visits) and increases the probability of infection. Actually, there is an incidence of infection related mainly to the long period of insertion in the cervical canal.

(3) Relatively low swelling pressure causes that end protruding into uterus to swells faster, and more than the main part of the insert in the cervical canal thereby causing difficulty in subsequent removal.

(4) Uniform swelling and considerable decrease of mechanical strength of maximally swollen *Laminaria japonica* prevents successful removal in some cases as the protruding ends of the device are rather soft and slippery.

(5) Shortage of supply is another disadvantage.

(6) The diameter of the device is rather uneven and of the commercially available plant varies from about 2 to 4 mm. Often 3 to 6 of the laminaria are used simultaneously to obtain an adequate dilation, mainly in cases of advanced pregnancy termination.

(7) As the device is produced from the natural raw materials, it must be hand-made contributing to high prices.

OBJECTS OF THE PRESENT INVENTION

An object of the present invention is to provide a novel device for dilating the cervical channel obviating the problems of natural dialators.

SUMMARY OF THE INVENTION

These and other objects of the present invention are achieved by a cervical canal dilating device having an essentially cylindrically shaped stem formed in major portion thereof of a dehydrated hydrogel having a swelling capacity of $V_2 = 0.01$ to $0.25$ and having an enforced uniaxial deformation of at least 1.1 and sized to a diameter of from 2 to 10 mm, and to a length of from 35 to 150 mm.

BRIEF DESCRIPTION OF THE DRAWINGS

A better understanding of the present invention as well as other objects and advantages thereof will become apparent upon consideration of the detailed disclosure thereof, especially when taken with the accompanying drawings, wherein like numerals designate like parts throughout, and wherein.

DETAILED DESCRIPTION OF THE INVENTION

Figure 1:
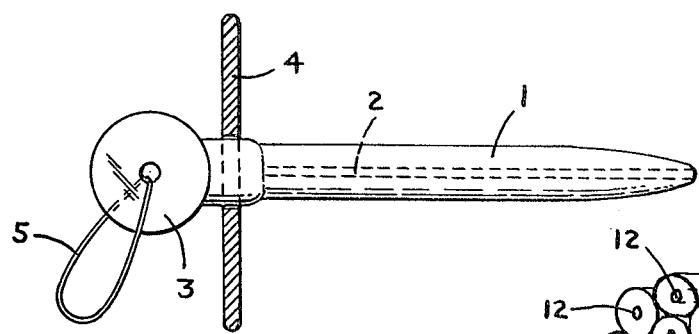
FIG. 1 is a schematic elevational view partial in section, of one embodiment of the present invention.
Figure 2:
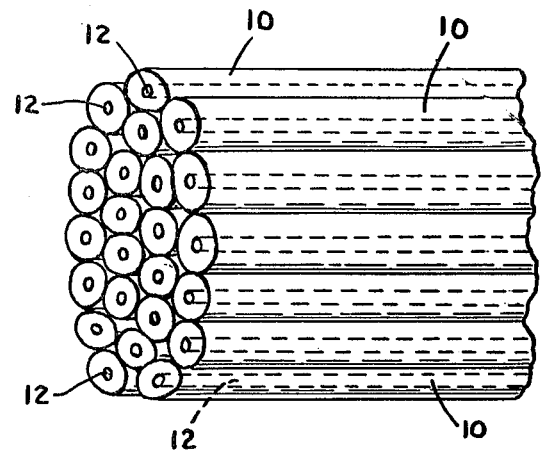
FIG. 2 is an enlarged view of another embodiment of the present invention.

Referring now to FIG. 1, there is illustrated one embodiment of the present invention comprised of a stem 1 formed about a reinforcing core 2 having a flat end 3, a collar 4 and a handle 5. In FIG. 2, there is illustrated another embodiment of the present invention comprised of a plurality of stems 10 each formed about a re-enforcing core 12.

The medical device of the present invention is essentially cylindrically-shaped and of a diameter of 2 to about 10 mm. and preferrably 2.5 to 6. mm. and of a length of 35 to 150 mm., preferably 40 to 75 mm. and comprised of a dehydrated synthetic hydrogel having swelling capacity $v_2 = 0.01$ to $0.25$ and having an enforced uniaxial deformation $E_{enf} \geq 1.1$. The swelling capacity of the hydrogel is expressed by volume fraction of dry polymer in hydrogel swollen to equillibrium with pure water at 25° C.

Therefore, $$V_2 = V_d/V_{sw},$$

where $V_d, V_{sw}$ = volumes of dry and swollen hydrogel, respectively.

The enforced deformation is given by:

$$E_{enf} = L_o/L_{di},$$

where $L_o$ = length of cylindrical portion containing the hydrogel, and $L_{di}$ = length of same cylindrical portion of hydrogel in dry isotropic state.

Therefore, the hydrogel is deformed along the axis of the cylindrically-shaped portion of the device, and its deformation cannot be relaxed without a change of conditions, such as increase of temperature or hydration of the gel. The deformation can be maintained in the hydrogel by various means which will be hereinafter described, the enforced deformation of the hydrogel is a significant feature of the present invention.

The importance of enforced deformation is obvious from its relation to the deformation introduced by isotropic swelling, i.e.

$$E_{si} = L_{si}/L_{di} = 1/\sqrt[3]{v_2},$$

where $L_{si}, L_{di}$ = linear dimensions of isotropically swollen and isotropically dry hydrogel.

The ratio of swollen and dry diameter is the target parameter and is given by:

$$\phi = D_{sw}/D_d = E_{si}\sqrt{E_{enf}} = \sqrt{E_{enf}}/\sqrt[3]{v_2}$$

The desirable high value of $\phi$ can be achieved by both high $E_{enf}$ and by low $v_2$. A low value of $v_2$ is however, accompanied by a steep decrease in mechanical strength, decrease of modulus of elasticity, whereas $E_{enf}$ is independent of such properties.

Another important property of the hydrogel is swelling pressure, since the device is designed to perform work against outer pressure. The swelling pressure steeply decreases with decreasing $v_2$, and is closely related to the modulus of elasticity in the swollen state. It is desirable to achieve a high value of $\phi$ at as high value of $v_2$ as practicable.

Still another important aspect of the problem is final length of the swollen device, i.e., axial deformation ($E_{ax} = L_{sw}/L_o$), given by:

$$E_{ax} = E_{si}/E_{enf} = 1/(E_{enf}\sqrt[3]{v_2})$$

Ratio of changes of diameter to length by swelling in given by $$R = \phi/E_{ax} = (E_{enf})3/2,$$

and is another measure of the device anisotropy. It is obvious that without the enforced deformation ($E_{enf} = 1$), the length of the device increases in the same degree as its diameter during swelling.

The following Table I illustrates the importance of the enforced deformation from a comparison of performance of 3 hypothetical hydrogel cylinders of an original length 50 mm. and a diameter 3 mm. to be swollen to a diameter of 9 mm.

TABLE I

| $E_{enf}$ | 1.00 | 2.08 | 2.41 |
|---|---|---|---|
| Final length: | 150 | 50 | 40 |
| Final $v_2$ | 0.012 | 0.11 | 0.14 |

The dilation of a given cervix from 3 to 9 mm. demands a certain work which is proportional to the final swelling pressure related to tissue resistance. Therefore, the same swelling pressure has to be achieved at $v_2 = 0.012$, 0.11 and 0.14, in the above three examples, respectively. There is no known synthetic hydrogel which could deliver the necessary swelling pressure at 1% of dry polymer in the swollen gel as in the first case ($v_2 = 0.012$), but there are various polymers which may do the job at 10 or 15% of dry substances ($V_2 = 0.11-0.14$). Therefore, the enforced deformation is a paramount feature of the present invention, while polymer composition, methods for introduction and maintenance of enforced deformation as well as the device design are secondary feature.

The hydrogels of the present invention contain a substantial amount of ionizable groups, particularly carboxylates, sulfo-groups, sulfate groups, sulfamide groups, primary, secondary or teriary amines, nitrogen-containing heterocycles and their quaternary derivatives. Also non-ionizable hydrophylic groups, such as hydroxy, amide and N-substituted amide groups, urethane groups, esteric groups, hydrazides and N-substituted hydrazides and hydroxamide groups may be present either alone or in combination with the ionizable groups.

A most preferred hydrogel is derived from polyacrylonitrile and containing a major portion of acrylamide and acrylic acid units, and a minor portion of residual acrylonitrile units, preferrably arranged in crystallizable sequences.

The hydrogel can be sparingly crosslinked by a minor amount of polyfunctional comonomer added to the polymerization mixture, or by known crosslinking reactions on the finished polymers. Crossliking is advantageous in some instances because of the additional deformation energy introduced with enforced deformation.

Another aspect of the present invention is that the hydrogel may be formed about a longitudially oriented single of multiple reinforcing element embedded in and firmly adhering to the hydrogel. The reinforcing element or elements are formed of a material which are substantially less swellable and of a higher modulus of elasticity than the hydrogel in the swollen state. Examples of such materials are threads of fibres of polyester, polyacrylonitrile, polyamide, polyurethanes, polypropylene, polyethylene or polystyrene in a stick, helix, mesh or otherwise shaped-elements. A preferred reinforcing element is one having limited extendability and good adhesion to the hydrogel.

The reinforcing elements have two functions, i.e. to increase mechanical strength in a swollen state, particularly important during the device removal, and to limit longitudinal swelling of the hydrogel so that swelling is utilized for dilation.

The reinforcing element introduces some tension into the hydrogel, decreases the overall swelling and decreases the mechanical strength of hydrogel itself. This is why tension is to be at least partially compensated by enforced deformation in opposite direction. Combination of the enforced deformation in the hydrogel and the reforcement by the longitudially oriented elements is another consideration of the present invention.

The reinforcing element can be made of like polymeric material as the hydrogel but with different composition and with lower swelling capacity. Like composition and partial swelling of the reinforcing elements provide perfect adhesion and relief of internal stress in the swollen hydrogel. It is particularly advantageous if the swellng gradually increases in the direction from the core toward the outer layer of the cylindrically-shaped portion so that internal stress is distributed. The hydrolysis of an acrylonitrile-containing composition is particularly suitable to this end.

The reinforcing element can be embedded in the hydrogel in various ways. For instance, the reinforcing element can form a core by the cylindrical part, particularly with the swelling gradient between the core and hydrogel as explained above. Another possibility is that the reinforcing elements, in form of fine fibres, are evenly distributed in the hydrogel. Still another possibility is a mesh of fibres and hydrogel foil wrapped in several layers in cigar-like fashion.

Enforced deformation can be introduced into the hydrogel by several methods. One method is heating the dry hydrogel above its glass transition temperature ($T_g$), stretching it in the rubbery state to the desired length and cooling below $T_g$ in the extended state. The enforced deformation is then frozen into the hydrogel until reaching the rubbery state either by swelling or by increased temperature or both.

In the event the hydrogel is reinforced by a less swellable and stronger element as described above, it is advantageous to carry out stretching at a temperature which is above $T_g$ both of the hydrogel and the reinforcing element. Both materials are simultaneously extended and the interfacial tension between the two materials during swelling is eliminated. The reinforcing material helps to preserve the enforced deformation.

A second method for enforced deformation is by drying the hydrogel under tension, and maintaining the length constant during drying. The swollen hydrogel is held in claims either in the relaxed state or under moderate stress, and dryed by hot air in such state. The extention of the hydrogel by swelling is automatically compensated by the corresponding relaxation of the enforced stress. Another aspect of the present invention, is to provided the device with a non-swellable handle which is advantageously flat and connected to the reinforcing elements. The handle facilitates insertion and safe removal of the device. The handle can be provided with a thread to further facilitate removal. The handle has substantially larger dimension than the swellable part. It can be enlarged either in the flat portion or it can be provided by a collar made of a suitable plastic, e.g. polypropylene. A disc or collar may be either loose on the handle or firmly attached thereto. The enlarged dimension in either way prevents excessive insertion into the cervical canal.

Various examples of the device design, all utilizing the principles described above, are described in the following examples, which are intended not to limit the herein described invention.

EXAMPLE 1

A polyelectrolyte complex hydrogel consisting of mixture of poly(vinylsulfonic acid) and quaternized poly(vinylpyrrolidone) with swelling capacity $v_2=0.2$ is extruded to form a stick 12.5 mm, in diameter in the swollen state, fastened into clamps under moderate tension and dried by hot air. The dry stick is cut into sections 70 mm. long. 10 mm. end parts of each was pressed by hot pliers and cooled. A hole 2 mm. in diameter is drilled into the thus formed flat ends and provided with loop of a polyamide thread.

EXAMPLE 2

A mixture of 60 parts by weight of 2-hydroxyethyl methacrylate, 40 parts by weight of N,N-dimethylacrylamide, 1 part by weight of ethyleneglycol dimethacrylate and 0.2 parts by weight of benzoylperoxide is prepared. A cylindrical glass mold is filled with crimped polyester fibres and the monomer mixture added so that about 10 mm of the fibres protruded above its level. The mixture is then polymerized under a nitrogen blanket at 80° C. A mixture of 80 parts by weight of methylmethacrylate, 20 parts by weight of glycidyl methacrylate and 0.5 parts of benzoyl peroxide is added to the mold in an amount sufficient to cover the protruding fibres and the polymerization procedure repeated. The mold is destroyed and the stick is heated to 125° C. and stretched in a pair of cold pliers by about 50%. The hydrogel flat end is cut off, leaving a hydrogel cylinder reinforced by the polyester fibres combined with a flat non-swellable handle with similar reinforcement.

EXAMPLE 3

50 parts by weight of acrylonitrile and 0.2 parts by weight of ammonium persulphate is admixed into 50 parts by weight of 65% nitric acid. The mixture is filled into glass tubes, sealed and heated to 40° C. for 50 hours. The polymerized rubbery sticks are then removed from the tubes and immersed in an excess of 5% solution of NaOH for 70 hours at 18° C. The thus formed hydrogel rods are thoroughly washed and dried. The dry sticks are then heated in parrafin oil to 140° C., stretched to 2.5 of their dry length and cooled. The swelling capacity of the hydrogel is $v_2=0.1$, and of a tensile strength sufficient for the purpose even without reinforcement.

EXAMPLE 4

A mixture of 52.5 parts by weight of acrylonitrile, 47.5 parts by weight of 70% nitric acid and 0.01 parts by weight of ammonium persulphate is heated 72 hours to 40° C. in cylindrical molds. The polymerized mixture is removed, washed and cut into sticks 60 mm. long. 7.5 mm. of each side of a stick is flattened in a hydraulic press, covered by a rubber jacket and put into a sodium hydroxide solution for 15 hours. After thorough washing, the sticks are comprised of a highly swellable hydrogel jacket and of a less swellable, flexible core. The flat ends protected by rubber are essentially non-swellable. The sticks are fastened by both flat ends and dryed at moderate tension. The dry sticks are cut in half yielding two devices from each stick as illustrated in FIG. 1.

EXAMPLE 5

Polyacrylonitrile is dissolved in nitric acid, and partially hydrolyzed to a hydrogel having $v_2=0.22$. Another part of polyacrylonitrile is similar hydrolyzed at lower temperature, yielding hydrolyzate with 30% water. The viscous solutions of both hydrolysates are co-extruded into a water coagulation bath to a thin wire having a core of the less hydrolyzed and a jacked of the more hydrolyzed polymer. The washed wires are assembled into cylindrical clusters, pressed together by a hot cylindrical dye and dried. The dry cluster is heated to 125° C., extended 3.5 times and cut into 100 mm. stick after cooling as illustrated in FIG. 2.

EXAMPLE 6

Figure 3:
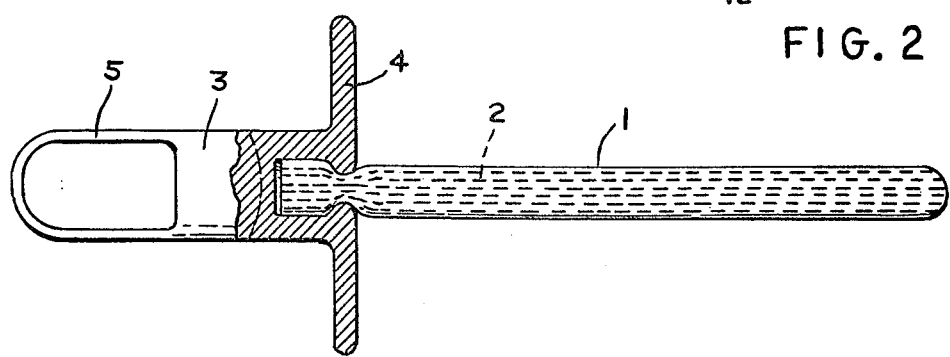
FIG. 3 is schematic elevational view, partially in section of another embodiment of the present invention.

Extruded foil of modified polyacrylonitrile hydrolyzate containing a minor portion of nitrile groups and a major portion of acrylamide units and N-sulfoethylacrylamide units is covered by flexible polyethylene terephthalate mesh and rolled in cigar-like fashion and dried. The multilayer stick is elongated at 140° C. to double its dry length. One end of each stick is inserted into a molding cavity in which is injection-molded polypropylene, an end including a collar and a thread loop for easy handling and removal as depicted in FIG. 3.

EXAMPLE 7

Figure 4:
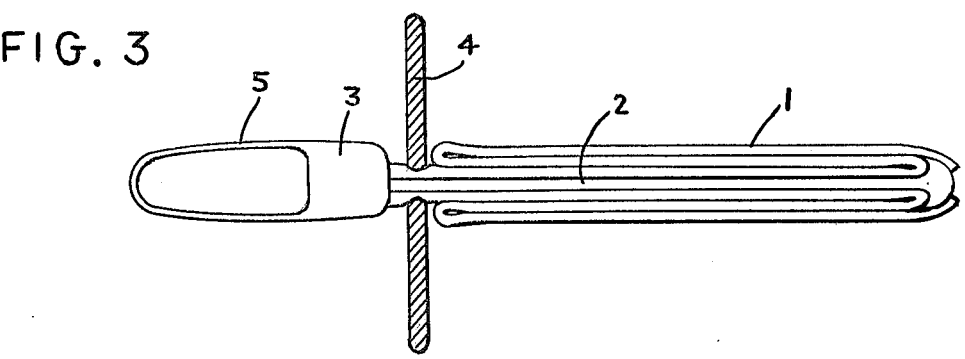
FIG. 4 is a schematic elevational view, partially in section, of still another embodiment of the present invention.

A tube of the hydrogel from Example 6 is folded placed on a 6-polyamide core having a handle and dried. The dry stick is heated to 155° C. and extended 2.8 times and is illustrated in FIG. 4.

EXAMPLE 8

Figure 5:
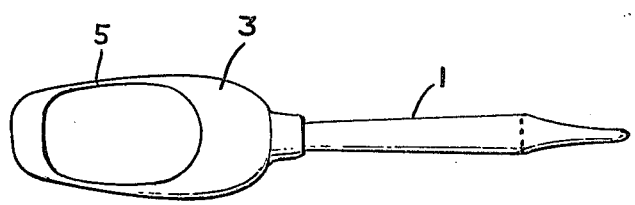
FIG. 5 is a schematic elevational view, partially in section of a further embodiment of the present invention.

A block copolymer containing acrylonitrile sequences and a substantial portion of glutarimide groups is molded into the shape of a cylindrical stem having two enlarged flat ends. The cylindrical central part is treated with an aqueous solution of sodium salt of taurine for several hours yielding a highly swellable hydrogel ($v_2=0.15$). The molding is washed, and the non-swellable flat ends clamped. The hydrogel stem is dried by warm air in a moderately extended state. The dry piece is cut in half to yielding 2 dilators as depicted in FIG. 5.

What is claimed:

1. A device for dilation of a cervix by swelling comprised of an essentially cylindrically-shaped stem of 2 to 10 mm in diameter and 35 to 150 mm in length, said stem formed of at least a major portion of a dehydrated hydrogen having a swelling capacity of 0.01 to 0.25 and an enforced uniaxial deformation of at least 1.1.

2. The device in the claim 1 wherein said hydrogel has an enforced deformation of 0.75 to 1.25 times linear isotropic swellng deformation of said hydrogel.

3. The device according to the claim 1 wherein the said hydrogel contains a substantial concentration of ionizable functional groups.

4. The device according to claim 3 wherein said ionizable groups are selected from the groups consisting of $CO.OX$, $SO_3X$, $—O.SO_3X$, $—C(=N—OH)OH$, $NRR'$, $—NRRR''$, pyrridyl or quarternized pyrridyl, where X is hydrogen, metal cation of N-containing cation and R, R' and R" are hydrogen, alkyl or substituted alkyl $C_1$ to $C_6$ with O or N atoms.

5. The device according to claim 1 wherein said hydrogel contains hydrophylic groups selected from a group consisting of amide, N-alkylamide, N,N-dialkylamide, $—CO:NH:NHR$, cyclic lactames, cyclic lactones and acrylic esters of polyhydroxycompounds.

6. The device according to the claims 1, 3 or 5 wherein said hydrogel is derived from partially hydrolyzed polyacrylonitrile.

7. The device according to the claim 1 wherein said hydrogel is reinforced by a single element or multiple elements from a material substantially less swellable than said hydrogel.

8. The device according to claim 7 wherein said reinforcing element is oriented essentially along the longitudinal axis of said stem.

9. The device according to claim 8 wherein an end of said stem is flat and its dimension lateral to said longitudinal axis is larger than the diameter of said stem.

10. The device according to claims 7 wherein said reinforcing element adheres to said hydrogel in a swollen state.

11. The device according to claim 10 wherein said hydrogel and said reinforcing element are connected by a layer with a swelling capacity increasing from said reinforcing element to said hydrogel.

12. The device according to claim 7 wherein said hydrogel and the reinforcing element are connected by a layer with a swelling capacity increasing from said reinforcing element to the said hydrogel.

13. The device according to claim 1 wherein an end of said stem is made of material is substantially less swellable than said hydrogel.

14. The device according to claim 13 wherein said hydrogel is reinforced by a single element or multiple elements from a material substantially less swellable than said hydrogel and said less swellable end is connected to said reinforcing element.

* * * * *